(12) United States Patent
Li et al.

(10) Patent No.: US 6,201,158 B1
(45) Date of Patent: Mar. 13, 2001

(54) PROCESS FOR MAKING INTERMEDIATE ALDEHYDES

(75) Inventors: Zhen Li; Ann Decamp, both of Scotch Plains; Veena Upadhyay, Westfield, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/321,008

(22) Filed: May 27, 1999

Related U.S. Application Data

(60) Provisional application No. 60/090,206, filed on Jun. 22, 1998.

(51) Int. Cl.[7] .................................................. C07C 33/28
(52) U.S. Cl. .......................... 568/813; 546/344; 548/570; 568/874
(58) Field of Search ..................................... 568/874, 813; 546/344; 548/570

(56) References Cited

U.S. PATENT DOCUMENTS

| | | | |
|---|---|---|---|
| 4,309,438 | 1/1982 | Christensen et al. | |
| 4,479,947 | 10/1984 | Christensen et al. | |
| 5,292,929 | * 3/1994 | Sullivan | 568/874 |
| 6,015,926 | * 1/2000 | Chen | 568/813 |

OTHER PUBLICATIONS

Noyori, R., et al., *Angewandte Chemie Int. Ed.*, 30, 49–68, (1991).
Soai, K., et al., *Chemical Review*, 92, 833–856, (1992).
Seiji, N. et al., *J. of Chemical Society Perkin Trans.*, 1, 937–943, (1990).
Ramos Tombo, G.S., et al., *Synlett*, 547, (1990).
Thompson, A., et al, *Tetrahedron Letters*, 36, 8937–8940, (1995).
Huffman, M., et al, *J. of Organic Chemistry*, 60 (6), 1590–1594 (1995).
Miyuki, I. et al., *Tetrahedron Assymetry*, 5, No. 10, 1901–1904 (1994).
Corey, E. J., et al., *J. of American Chemical Society*, 116, 3151–3152, (1994).

* cited by examiner

*Primary Examiner*—Michael L. Shippen
(74) *Attorney, Agent, or Firm*—James M. Hunter, Jr.; Mark R. Daniel

(57) ABSTRACT

The present invention relates to a process for making propargylic alcohols by zinc-mediated catalytic, asymmetric addition of acetylenes to aldehydes.

The compounds are represented by formula I:

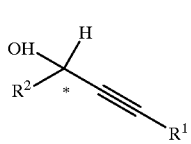

13 Claims, No Drawings

PROCESS FOR MAKING INTERMEDIATE ALDEHYDES

This application claims benefit of Provisional application 06/090,206, filed Jun. 22, 1998.

BACKGROUND OF THE INVENTION

The invention disclosed herein concerns a process for making propargylic alcohols by zinc-mediated catalytic, asymmetric addition of acetylenes to aldehydes. Enantioselective addition of organometallic reagents to aldehydes affords optically active secondary alcohols. Such optically active secondary alcohols serve as intermediates in many naturally occurring compounds, biologically active compounds, and materials such as liquid crystals. The resultant alcohols are also important as synthetic intermediates of various fuctionalities which include halide, amine ester and ether.

Various publications of related zinc mediated and zinc acetylide procedures have been cited in the literature. See Noyori, R., et al., *Angewandte Chemie Int. Ed.*, 30, 49–68, (1991); Soai, K., et al., *Chemical Review*, 92, 833–856, (1992); Seiji, N. et al., *J. of Chemical Society Perkin Trans.*, 1, 937–943, (1990); Ramos Tombo, G. S., et al., *Synlett*, 547, (1990); Thompson, A., et al, *Tetrahedron Letters*, 36, 8937–8940, (1995); Huffman, M., et al, *J. of Organic Chemistry*, 60 (6), 1590–1594 (1995); Miyuki, I. et al., *Tetrahedron Assymetry*, 5, No. 10, 1901–1904 (1994); and Corey, E. J., et al., *J. of American Chemical Society*, 116, 3151–3152, (1994).

In the past, asymmetric acetylide additions to carbonyl compounds were performed in either of two ways, stoichiometrically or catalytically. In the stoichiometric case, a large amount of the chiral ligand is required. Even with high enantiomeric excess (ee), this is undesirable from the point of view of cost and additional equipment needed to recover the ligand. In addition, many methods use the intermediacy of a strong base to generate an acetylide species, leading to limits on the functionality present in the substrates.

In the catalytic cases reported, the enantiomeric excesses obtained have been low. In addition, the reported procedures use a two-fold excess of a difficult to prepare diacetylenic zinc species. In effect, three acetylene groups are discarded. Although this particular catalytic methods produces high % ee, this method is limited in that a preformed dialkylzinc species must be used.

The disadvantages of the processes employed in the prior art are the use of a stoichiometric quantity of a chiral ligand or in the catalytic mode, the preformation of a diacetylenic zinc species.

The advantages of the process employed in the present invention include:

(1) no preformation of zinc reagents, the free acetylene is used in the reaction.

(2) a catalytic quantity, typically 10 mole %, of the chiral ligand is used.

(3) ee's are moderate to high.

The invention disclosed herein provides a process for the catalytic asymmetric addition of substituted acetylenes to aldehydes, furnishing propargylic alcohols in moderate to high ee.

SUMMARY OF THE INVENTION

An acetylene, a dialkylzinc, and a catalytic amount of chiral ligand, are reacted and added to an aldehyde, to form a propargylic alcohol product in moderate to high % ee. The fundamental principle involves the novel mode of formation of the asymmetric zinc acetylenic intermediate that adds to the aldehyde. Direct exposure of the acetylene to dialkylzinc in the presence of a catalytic amount of a chiral aminoalcohol ligand generates a reactive, asymmetric zinc acetylide species, rendering the reaction catalytic in the chiral ligand.

The generation of the reactive asymmetric zinc acetylide reagent can be generally be carried out in from about 5 minutes to 1 hour at temperature of from about 0° C. to about 30° C. The addition of the asymmetric zinc acetylenic reagent to the aldehyde can generally be carried out over a period of about one hour to about twenty-four hours at temperatures of from about −70° to room temperature.

In one embodiment of the invention a process of synthesizing a compound of formula (I) is described:

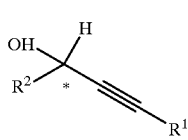

(I)

wherein $R^1$ represents aryl, alkyl, alkynyl, alkylsilyl, ester or ether; said aryl, alkyl and alkynyl being optionally substituted with one to three groups selected from $R^a$, $R^2$ is aryl or $C_{1-6}$ alkyl; said aryl and $C_{1-6}$ alkyl being optionally substituted with one to three groups selected from $R^a$, comprising:

reacting a compound of formula (II):

(II)

wherein $R^1$ is defined above;
with a compound of formula (III):

R Zn R  (III)

wherein, R is $C_{1-6}$ alkyl or aryl;
in the presence of a chiral ligand of formula (IV) at a temperature of about 0° C. to about 30° C.:

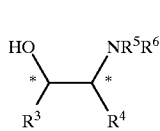

(IV)

wherein, $R^3$ and $R^4$ are independently aryl, alkylaryl, alkyl, or H; said aryl, akylaryl and alkyl being optionally substituted with one to three groups of $R^a$, or $R^3$ and $R^4$ together can form a 5- or 6-membered ring, which can be optionally substituted with one to three groups of $R^a$;
$R^5$ and $R^6$ are independently, H, alkyl, aryl, said alkyl and aryl being optionally substituted with one to three groups of $R^a$, or $R^5$ and $R^6$ together with the N atom to which they are attached form a 5- or 6-membered heterocyclic ring, which can be optionally substituted with one to three groups of $R^a$ and;
$R^a$ is H, $C_{1-10}$ alkyl, halogen, $NO_2$, OR, —NR, $C_{5-10}$ aryl or $C_{5-10}$ heteroaryl;
adding the resultant mixture to a compound of formula (V) at a temperature of about −70° C. to room temperature:

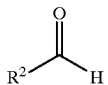

wherein, $R^2$ is defined above to produce a compound of formula (I).

DETAILED DESCRIPTION OF THE INVENTION

The invention is described herein in detail using the terms defined below unless otherwise described.

The asterisk symbol (*) represents asymmetric carbon atoms or asymmetric centers. The compounds of the present invention may contain one or more asymmetric carbon atoms and may exist in racemic and optically active forms. All of these compounds are contemplated to be within the scope of the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention.

The term "alkyl" refers to a monovalent alkane (hydrocarbon) derived radical containing from 1 to 10 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopropyl, cyclobutyl, cycloheptyl, cyclopentyl and cyclohexyl. When substituted, alkyl groups may be substituted with up to three substituent groups, selected from $R^a$ as defined, at any available point of attachment. When the alkyl group is said to be substituted with an alkyl group, this is used interchangeably with "branched alkyl group."

Aryl refers to 5–10 membered aromatic rings e.g., phenyl, substituted phenyl and like groups as well as rings which are fused, e.g., naphthyl and the like. Aryl thus contains at least one ring having at least 5 atoms, with up to two such rings being present, containing up to 10 atoms therein, with alternating (resonating) double bonds between adjacent carbon atoms. The preferred aryl groups are phenyl and naphthyl. Aryl groups may likewise be substituted with one to three groups of $R^a$ as defined herein. Preferred substituted aryls include phenyl and naphthyl substituted with one or two groups.

The term "alkylaryl" refers to an alkyl that is covalently joined to an aryl group.

The term heteroaryl or heterocyclic, as used herein except where noted, represents a stable 5- to 7-membered mono- or bicyclic or stable 7- to 10-membered bicyclic heterocyclic ring system, any ring of which may be saturated or unsaturated, and which consists of carbon atoms and from one to three heteroatoms selected from the group consisting of N, O and S, and in which one or two additional carbon atoms is optionally replaced by a heteroatom selected from O or S, and in which from 1–3 addtional carbon atoms are optionally replaced by nitrogen heteroatoms, and including any bicyclic group in which any of the above-defined heterocyclic rings is fused to a benzene ring. The heterocyclic ring may be attached at any heteroatom or carbon atom which results in the creation of a stable structure. The heteroaryl or heterocyclic may be substituted with one to three groups of $R^a$. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofaryl, tetrahydropyranyl, thiophenyl, imidazopyridinyl, tetrazolyl, triazinyl, thienyl, benzothienyl, thiamorpholinyl sulfoxide, thiamorpholinyl sulfone, and oxadiazolyl.

The term "halogen" is intended to include the halogen atom fluorine, chlorine, bromine and iodine.

The term "alkynyl" refers to a hydrocarbon radical straight or branched, containing from 2 to 10 carbon atoms and at least one carbon to carbon triple bond. Preferred alkynyl groups include ethenyl, propynyl and butynyl.

The term alkylsilyl refers to ethylsilyl, methylsilyl, triethylsilyl, trimethylsilyl, tributylsilyl, t-butyldimethylsilyl and the like.

The pharmaceutically acceptable esters would are such as would be readily apparent to a medicinal chemist, and include for example those described in U.S. Pat. No. 4,309,438. Included within such pharmaceutically acceptable esters are those which are hydrolyzed under physiological conditions, such as pivaloyloxymethyl, acetoxymethyl, pthalidyl, indanyl and methoxymethyl, and others described in detail in U.S. Pat. No. 4,479,947.

The term ether is intended to include tetrahydrofuran, tetrahydropyran, 1–4-dioxane, diethyl ether, ethyl methyl ether, diphenyl ether, t-butyl methyl ether, dipropyl ether, p-bromophenyl ethyl ether, ethylene glycol dimethyl ether, t-butyl ethyl ether, ethyl phenyl ether, allyl phenyl ether, methyl propyl ether, diallyl ether and the like.

The starting materials (organozinc, benzaldehyde, napthaldehyde and phenylacetylene) used in the process are commercially available from Aldrich Chemicals.

Solvents generally used in this reaction scheme are toluene and tetrahydrofuran (THF), hexane, cyclohexane, benzene, hexene, dimethyl formamide (DMF), ether, dipropyl ether, ethanol, tetrahydropyran, 1,4-dioxane, 1,2-dimethoxyethane or mixtures thereof. Preferred solvents for the addition reaction are toluene and THF.

Examples of suitable R groups are $C_{1-6}$ alkyl or aryl. Preferred R groups are $C_{1-2}$ alkyl and diphenyl. Examples of suitable $R^1$ groups are substituted $C_{1-6}$ alkyl and aryl groups, such as phenyl, napthyl, alkylsilyls, such as trimethylsilyl, esters, such as tert-butyl propiolate and ethers such as tetrahydrofuran and tetrahydropyran.

Additional examples of $R^1$ groups include alkynes, such as 1-pentyne, ethyl ethynyl ether and ethynyl p-tolyl sulfone.

Examples of suitable ligands for the synthesis process include the bidentate, tridentate, multidentate ligands, and tertiary and secondary amino alcohol ligands. A particular multidentate ligand that would result in ee's $\geq 50$ has the following structure:

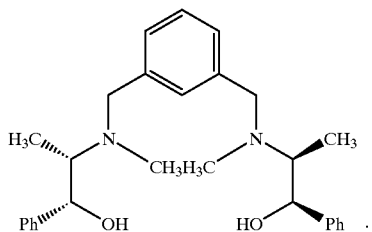

The above multidentate can be prepared using the method of Williams, D. R. and Fromhold, M. G., *Synlett*, 523–524 (1997). Other amino alcohols which can be used in this invention and are taught in literature are the homogeneous chiral catalyst, which include the β- amino alcohols derived from (S)-proline, (S)-leucinol, prolinol derived, camphor derivatives, ephedrine and norephedrine derivatives and. Examples of other homogeneous chiral ligands include, chiral 1–2-diol, chiral oxazaborolidine, and transition metals complexed with chiral ligand. Examples of heterogeneous chiral catalysts include polymer supported chiral catalysts and silica gel or alumina supported chiral catalysts. Preferred ligands for the invention are amino alcohols, such as (1S, 2R)-2-N-pyrrolidinylamino-1, 2-diphenylalcohol and erythro-2-(pyrrolidinylamino)-1,2-diphenylethanol.

Examples of suitable aldehydes are substituted and unsubstituted aldehydes belonging to the group consisting of benzaldehyde, napthaldehyde, heteroaldehydes, or $C_{1-6}$ alkyl straight or branched chain aldehydes. The aldehydes are optionally substituted with one to three groups of halo, $C_{1-6}$ alkyl, and $NO_2$. Preferred substituted aldehydes are chloro- and fluoro-benzaldehyde, 1-methyl-2-pyrrolcarboxyaldehyde, 2-pyridinecarboxyaldehyde and pivaldehyde.

The generation of the reactive asymmetric zinc acetylide reagent can be generally be carried out in from about 5 minutes to about 1 hour at temperatures of from about 0° C. to about 30° C. The addition of the asymmetric zinc acetylenic reagent to the aldehyde can generally be carried out over a period of about one hour to about twenty-four hours at temperatures of from about −70° to room temperature.

In a preferred embodiment of the invention herein, a process of synthesizing a compound of formula (VI) is described:

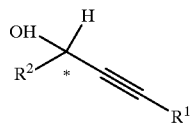

(VI)

wherein, $R^1$ is phenyl, $C_{1-2}$ alkyl, alkylsilyl or t-butyl propriolate ester and $R^2$ is $C_{6-10}$ aryl or $C_{1-4}$ alkyl comprising:
reacting a compound of formula (VII):

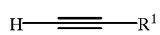

(VII)

wherein $R^1$ is defined above;
with a compound of formula (VIII):

R Zn R  (VIII)

wherein, R is $C_{1-2}$ alkyl;

in the presence of a chiral ligand selected from the group consisting of (1S, 2R)-2-N-pyrrolidinylamino-1, 2-diphenylalcohol and erythro-2-(pyrrolidinylamino)-1,2-diphenylethanol, adding the resultant mixture to an aldehyde compound selected from the group consisting of chloro- and fluoro-benzaldehyde, 1-methyl-2-pyrrolcarboxyaldehyde, 2-pyridinecarboxyaldehyde and pivaldehyde to produce a compound of formula (VI).

Compound (VI) can serve as useful intermediates in many naturally occurring compounds, biologically active compounds, and materials such as liquid crystals.

The invention is further described in connection with the following non-limiting example.

PREPARATIVE EXAMPLE

Preparation of Amino Alcohol Chiral Ligand

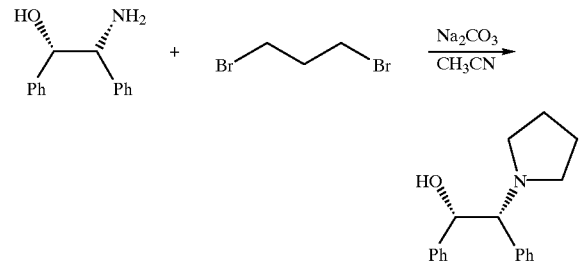

A 200 mL 3-neck round bottom flask with a thermocouple and a reflux condenser was charged with 60 mL acetonitrile. 1,4-dibromobutane (5.18 g, 24 mmol) and sodium carbonate (8.48 g, 80 mmol) were added. The solution was stirred for 10 min before the addition of (1S, 2R)-(−)-2-amino-1,2-diphenylethanol (4.27 g, 20 mmol). The reaction mixture was kept at reflux for 16 hours, and was then cooled to room temperature. Water (100 mL) and tert-butyl methyl ether (50 mL) were added. The organic and aqueous phases were separated, and the aqueous phase was extracted with tert-butyl methyl ether (3×250 mL). The combined organic phase was washed with brine (200 mL), dried over $MgSO_4$ and filtered. The solvent was removed under reduced pressure and the residue was recrystallized from hexane to afford the pure ligand in 84% yield.

EXAMPLE 1

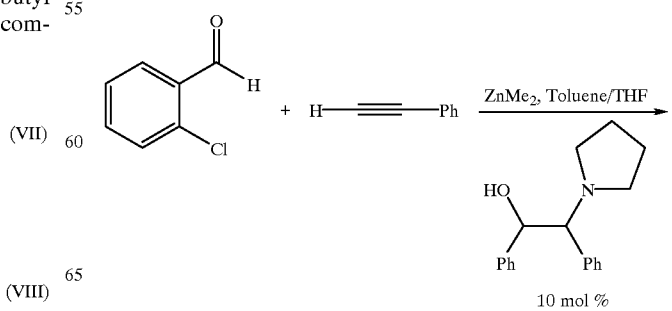

10 mol %

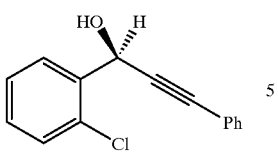

To a stirred solution of phenylacetylene (245.1 mg, 2.4 mmol) in 0.4 mL of THF at −20° C. was added dimethylzinc (1.10 mL, 2.4 mmol) via syringe under nitrogen. After 15 minutes, (1S, 2R)-2-N-pyrrolidinylamino-1,2-diphenylalchohol (53.4 mg, 10 mol %) was added. The resulting solution was stirred at −20° C. for 15 minutes, and 2-chlorobenzaldehyde (281.1 mg, 2 mmol) was added via syringe under nitrogen. The reaction mixture was stirred at −20° C. overnight. After quenching the reaction with methanol at −20° C. followed by an aqueous work-up, the corresponding alcohol was obtained in 81% ee and 77% yield.

EXAMPLE 2

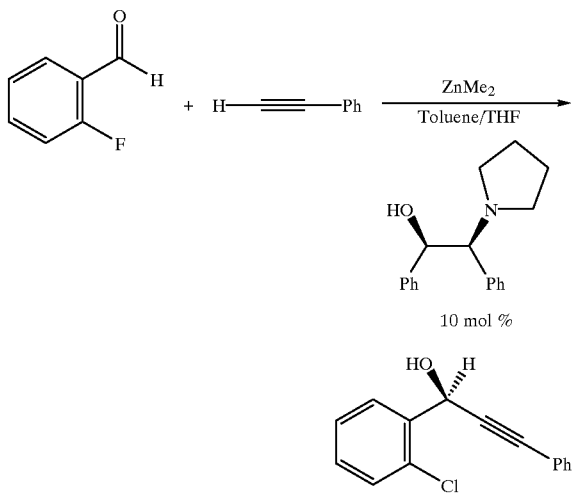

To a stirred solution of phenylacetylene (245.1 mg, 2.4 mmol) in 0.4 mL of THF at −30° C. was added dimethylzinc (1.10 mL, 2.2 mmol) via syringe under nitrogen. After 15 minutes, (1S,2R)-2-N-pyrrolidinylamino-1,2-diphenylalcohol (53.4 mg, 10 mol %) was added. The resulting solution was stirred at −30 ° C. for 15 minutes, and 2-florobenzaldehyde (248.2 mg, 2.0 mmol) was added via syringe under nitrogen. The reaction mixture was stirred at −30° C. overnight. After quenching the reaction with methanol at −30° C. followed by an aqueous work-up, the corresponding alcohol was obtained in 82% ee and 67% yield.

EXAMPLE 3

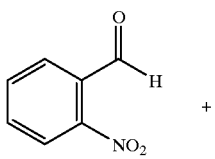

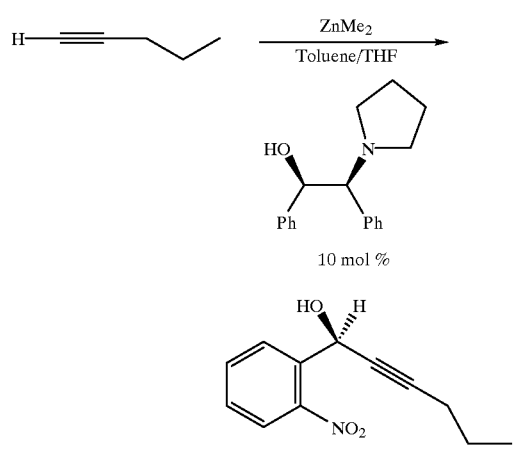

To a stirred solution of 1-pentyne (163.5 mg, 2.4 mmol) in 0.4 mL of THF at −20° C. was added dimethylzinc (1.10 mL, 2.2 mmol) via syringe under nitrogen. After 15 minutes, (1S, 2R)-2-N-pyrrolidinylamino-1,2-diphenylalcohol (53.4 mg, 10mol %) was added. The resulting solution was stirred at −20 ° C. for 15 minutes, and 2-nitrobenzaldehyde (302.2 mg, 2.0 mmol) was added via syringe under nitrogen. The reaction mixture was stirred at −20° C. overnight. After quenching the reaction with methanol at −20° C. followed by an aqueous work-up, the corresponding alcohol was obtained in 87% ee.

EXAMPLE 4

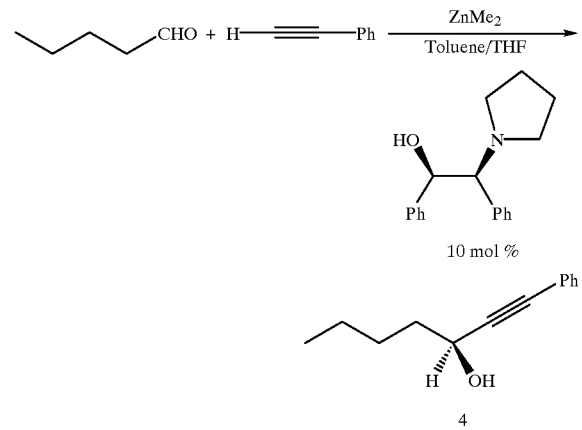

To a stirred solution of phenylacetylene(245.1 mg, 2.4 mmol) in 0.4 mL of THF at −20° C. was added dimethylzinc (1.10 mL, 2.2 mmol) via syringe under nitrogen. After 15 minutes, (1S, 2R) -2-N-pyrrolidinylamino-1,2-diphenylalcohol (53.4 mg, 10 mol %) was added. The resulting solution was stirred at −20° C. for 15 minutes, and valeraldehyde (172.3 mg, 2.0 mmol) was added via syringe under nitrogen. The reaction mixture was stirred at −20° C. overnight. After quenching the reaction with methanol at −20° C. followed by an aqueous work-up, the corresponding alcohol was obtained in 62% ee.

What is claimed is:

1. A method of synthesizing a compound of formula (I):

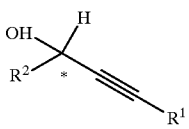

(I)

wherein $R^1$ represents aryl, alkyl, alkynyl, alkylsilyl, ester or ether; said aryl, alkyl and alkynyl being optionally substituted with one to three groups selected from $R^a$, $R^2$ is aryl or $C_{1-6}$ alkyl; said aryl and $C_{1-6}$ alkyl being optionally substituted with one to three groups selected from $R^a$, comprising:

reacting a compound of formula (II):

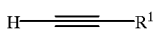

(II)

wherein $R^1$ is defined above;
with a compound of formula (III):

R Zn R     (III)

wherein, R is $C_{1-6}$ alkyl or aryl;
in the presence of a chiral ligand of formula (IV):

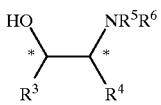

(IV)

wherein, $R^3$ and $R^4$ are independently aryl, alkylaryl, alkyl, or H; said aryl, akylaryl and alkyl being optionally substituted with one to three groups of $R^a$, or $R^3$ and $R^4$ together can form a 5- or 6-membered ring, which can be optionally substituted with one to three groups of $R^a$;

$R^5$ and $R^6$ are independently, H, alkyl, aryl, said alkyl and aryl being optionally substituted with one to three groups of $R^a$, or $R^5$ and $R^6$ together with the N atom to which they are attached form a 5- or 6-membered heterocyclic ring, which can be optionally substituted with one to three groups of $R^a$ and;

$R^a$ is H, $C_{1-10}$ alkyl, halogen, $NO_2$, OR, —NR, $C_{5-10}$ aryl or $C_{5-10}$ heteroaryl;

adding the resultant mixture to a compound of formula (V):

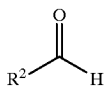

(V)

wherein, $R^2$ is defined above to produce a compound of formula (I).

2. The method of claim 1, wherein the reaction of formula (II) and (III) in the presence of the chiral ligand is at a temperature of about 0° C. to about 30° C.

3. The method of claim 2, wherein the resulting reaction mixture is added to compound (V) at a temperature of about −70° C. to room temperature.

4. The method of claim 1, wherein R is C1–6 alkyl.

5. The method of claim 4, wherein $R^1$ is aryl.

6. The method of claim 1, wherein $R^5$ and $R^6$ form a 5-membered heterocyclic ring.

7. The method of claim 6, wherein the 5-membered heterocyclic ring is pyrrolidine.

8. The method of claim 1, wherein $R^2$ is aryl.

9. The method of claim 8, wherein $R^2$ is an aryl group substituted with one to three groups of $R^a$.

10. The method of claim 9, wherein $R^a$ is a halogen.

11. The method of claim 10, wherein the halogen is chlorine or fluorine.

12. The method of claim 8, wherein $R^2$ is chloro benzaldehyde or fluoro benzaldehyde.

13. A method of synthesizing a compound of formula (VI):

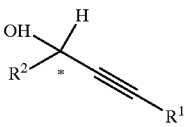

(VI)

wherein, $R^1$ is phenyl, $C_{1-2}$ alkyl, alkylsilyl or t-butyl propriolate ester and $R^2$ is $C_{6-10}$ aryl or $C_{1-4}$ alkyl comprising:

reacting a compound of formula (VII):

(VII)

wherein $R^a$ is defined above;
with a compound of formula (VIII):

R Zn R     (VIII)

wherein, R is $C_{1-2}$ alkyl;

in the presence of a chiral ligand selected from the group consisting of (1S, 2R)-2-N-pyrrolidinylamino-1, 2-diphenylalcohol and erythro-2-(pyrrolidinylamino)-1,2-diphenylethanol, adding the resultant mixture to an aldehyde compound selected from the group consisting of chloro- and fluoro-benzaldehyde, 1-methyl-2-pyrrolcarboxyaldehyde, 2-pyridinecarboxyaldehyde and pivaldehyde to produce a compound of formula (VI).

* * * * *